(12) United States Patent
Zhou

(10) Patent No.: US 9,676,834 B2
(45) Date of Patent: Jun. 13, 2017

(54) FIBULIN PROTEIN VARIANTS AND CORRESPONDING NUCLEIC ACID SEQUENCES

(71) Applicant: Yihong Zhou, Irvine, CA (US)

(72) Inventor: Yihong Zhou, Irvine, CA (US)

( * ) Notice: Subject to any disclaimer, the term of this patent is extended or adjusted under 35 U.S.C. 154(b) by 0 days.

(21) Appl. No.: 14/771,983

(22) PCT Filed: Apr. 1, 2014

(86) PCT No.: PCT/US2014/032597
§ 371 (c)(1),
(2) Date: Sep. 1, 2015

(87) PCT Pub. No.: WO2014/165552
PCT Pub. Date: Oct. 9, 2014

(65) Prior Publication Data
US 2016/0009775 A1    Jan. 14, 2016

Related U.S. Application Data

(60) Provisional application No. 61/807,445, filed on Apr. 2, 2013.

(51) Int. Cl.
*C07K 14/485* (2006.01)
*C07H 21/04* (2006.01)
*C07K 14/78* (2006.01)
*A61K 38/00* (2006.01)

(52) U.S. Cl.
CPC ............ *C07K 14/485* (2013.01); *C07K 14/78* (2013.01); *A61K 38/00* (2013.01)

(58) Field of Classification Search
None
See application file for complete search history.

(56) References Cited

U.S. PATENT DOCUMENTS

| 6,593,104 B1 * | 7/2003 | Stone | C07K 14/47 435/320.1 |
| 2002/0156263 A1 | 10/2002 | Chen et al. | |
| 2004/0191819 A1 | 9/2004 | Eveleigh et al. | |
| 2006/0094054 A1 * | 5/2006 | Schiemann | C12Q 1/6886 435/6.16 |

FOREIGN PATENT DOCUMENTS

WO    2012159085    11/2012

OTHER PUBLICATIONS

Hu et al., Cancer Res; 72(15):3873-3885, Aug. 1, 2012.3885.*
Yuan et al. "Isolation of cancer stem cells from adult glioblatoma multiforme," Oncogene, Dec. 16, 2004, vol. 23, pp. 9392-9400.

* cited by examiner

*Primary Examiner* — Marianne P Allen
(74) *Attorney, Agent, or Firm* — Riverside Law LLP

(57) ABSTRACT

Embodiments of the invention provide to fibulin 3 (also referred to as EGF-containing fibulin-like extracellular matrix protein 1 (EFEMP1)) polypeptide variants, and nucleotide sequences that code for them, characterized by having one or more activities of inhibiting cancer growth, inhibiting cancer cell invasion, and inhibiting cancer recurrence.

12 Claims, 10 Drawing Sheets

CLUSTAL W (1.83) multiple sequence alignment of three fibulins

```
SEQ ID NO:3 EFEMP1  ------------MLKALFLTMLTLALVKSQDTEETITYTQCTDGYEWDPVRQQCKDIDECDI
SEQ ID NO:4 EFEMP2  MLPCASCLPGSLLIWALLLLLLGSASPQDSEEPDSYTECTDGYEWDPDSQHCRDVNECLT
SEQ ID NO:5 FBLN5   ------MPGIKRILFVTILALCLPSPGN------AQAQCTNGFDLDRQSGQCLDIDECRT
                                                         :* *:**

SEQ ID NO:3 EFEMP1  VPDACKGGMKCVNHYGGYLCLPKTAQIIVNNEQPQQETQPAEGTSGATTGVVAASSMATS
SEQ ID NO:4 EFEMP2  IPEACKGEMKCINHYGGYLCLPRSAAVINDLHGE-----------------------
SEQ ID NO:5 FBLN5   IPEACRGDMMCVNQNGGYLCIPRTNPYTRGPYSN-----------------------
                    :*:**:* * *:*: ******:*:

SEQ ID NO:3 EFEMP1  GVLPGGGFVASARAVAGPEMQTGRNNFVIRRNPADPQRIPSNPSHRIQCAAGYEQSEHNV
SEQ ID NO:4 EFEMP2  ------------------------------GFPPPVFPAQHPNPCPPGYEPDDQDS
SEQ ID NO:5 FBLN5   ------------PYSTPYSGPYPAAAPPLSAPNYPTISRPLICRFGYQMDESNQ
                                                    * *:  . :.:

SEQ ID NO:3 EFEMP1  CQDIDECTAGTHNCRADQVCINLRGSFACQCPPGYQKRGEQCVDIDECTIPPYCHQRCVN
SEQ ID NO:4 EFEMP2  CVDVDECAQALHDCRPSQDCHNLPGSYQCTCFDGYRKIGPECVDIDECRYR-YCQHRCVN
SEQ ID NO:5 FBLN5   CVDVDECATDSHQCNPTQICINTEGGYTCSCTDGYWLLEGQCLDIDECRYG-YCQQLCAN
                    * *:***:  .::* *    *  :  * * *.** :   *:*****    :**: *.*

SEQ ID NO:3 EFEMP1  TPGSFYCQCSPGFQLAANNYTCVDINECDASNQCAQQCYNILGSFICQCNQGYELSSDRL
SEQ ID NO:4 EFEMP2  LPGSFRCQCEEPGFQLGPNNRSCVDVNECDMGAPCEQRCFNSYGTFLCRCHQGYELHRDGF
SEQ ID NO:5 FBLN5   VPGSYSCTCNPGFTLNEDGRSCQDVNECATENPCVQTCVNTYGSFICRCDPGYELERDGV
                    ****: *.*  ** *   .  * *:***   .* : * *  *  :*:*  ****  *

SEQ ID NO:3 EFEMP1  NCEDIDECRTSSYLCQYQCVNEPGKFSCMCPQGYQVVRS-RTCQDINECET-TNECREDE
SEQ ID NO:4 EFEMP2  SCSDIDECSYSSYLCQYRCVNEPGRFSCHCPQGYQLLAT-RLCQDIDECESGAHQCSEAQ
SEQ ID NO:5 FBLN5   HCSDMDECSFSEFLCQHECVNQPGTYFCSCPPGYILLDDNRSCQDINECEHRNHTCNLQQ
                     * *:***  *  :**:.***:**. **.**.**:: .  ::****:***  : * :

SEQ ID NO:3 EFEMP1  MCWNYHGGFRCYPRNPCQDPYILTPENRCVCPVSNAMCRELPQSIVTKYMSIRSDRSVPS
SEQ ID NO:4 EFEMP2  TCVNFHGGYRCVDTNRCVEFYIQVSENRCLCPASNPLCREQPSSIVHRYMTITSERSVPA
SEQ ID NO:5 FBLN5   TCYNLQGGFKCIDPIRCEEPYLRISDNRCMCPAENPGCRDQPFTILYRDMDVVSGRSVPA
                    * * ::**: *    ** :*:  : :**: **  .  *:*:*. *: *.: :**:*

SEQ ID NO:3 EFEMP1  DIFQIQATTIYANTINTFRIKSGNENGEFYLRQTSPVSAMLVLVKSLSGPREHIVDLEML
SEQ ID NO:4 EFEMP2  DVFQIQATSVYPGAYNAFQIRAGNSQGDFYIRQINNVSAMLVLARFVTGPREYVLDLEMV
SEQ ID NO:5 FBLN5   DIFQMQATTRYPGAYYIFQIKSGNEGREFYMRQTGFISATLVMTRFPLKGPREIQLDLEMI
                    *:**:***: *    :  *::**.  :** ** .:   :*:  .:  .***     ****:

SEQ ID NO:3 EFEMP1  TVSSIGTFRTSSVLRLTIIVGPFSF
SEQ ID NO:4 EFEMP2  TMNSLMSYRASSVLRLTVFVGAYTF
SEQ ID NO:5 FBLN5   TVNTVINFRGSSVIRLRIYVSQYPF
                    *:.: .  *  ***:** *  :  *
```

Figure 1A

| | | |
|---|---|---|
| EHR in Human EFEMP1 | QQETQPAEGTSGATTCVVAASSMATSGVLPGGGFVASAAAVAGPEMQTGRNNFVIRRNPA | SEQ ID NO:6 |
| EHR in Mouse EFEMP1 | MATSGVVPGGGFMASATAVAGPEVQTGRNNFVIRRNPA | SEQ ID NO:7 |
| EHR in Rat EFEMP1 | MATSGVIPGGGFIASATAVAGPEVQTGRNNFVIRRNPA | SEQ ID NO:8 |
| EHR in Human EGFRv1 | TTYQMDVNPEGKYSFGATCVKKCPRNYVVTDHGSCVRACGADSYEMEEDGVRKCKKCEGPCRKVCNGI | SEQ ID NO:9 |
| EHR in Human EFGRv2 | TTYQMDVNPEGKYSFGATCVKKCPRNYVVTDHGSCVRACGADSYEMEEDGVRKCKKCEGPCRKVCNGI | SEQ ID NO:10 |
| EHR in Human EGFRv3 | TTYQMDVNPEGKYSFGATCVKKCPRNYVVTDHGSCVRACGADSYEMEEDGVRKCKKCEGPCRAVCNGI | SEQ ID NO:11 |
| EHR in Human EGFRv4 | TTYQMDVNPEGKYSFGATCVKKCPRNYVVTDHGSCVRACGADSYEMEEDGVRKCKKCEGPCRKVCNGI | SEQ ID NO:12 |
| EHR in Human EGFRvIII | ----------KGNYVVTDHGSCVRACGADSYEMEEDGVRKCKKCEGPCRKVCNGI | SEQ ID NO:13 |

SEQUENCE LISTING

```
<160> NUMBER OF SEQ ID NOS: 13

<210> SEQ ID NO 1
<211> LENGTH: 386
<212> TYPE: PRT
<213> ORGANISM: Artificial sequence
<220> FEATURE:
<223> OTHER INFORMATION: Point mutated Homo sapiens

<400> SEQUENCE: 1

Met Asp Tyr Lys Asp Asp Asp Lys Leu Lys Ala Leu Phe Leu Thr
1               5                   10                  15

Met Leu Thr Leu Ala Leu Val Lys Ser Gln Asp Thr Glu Glu Thr Ile
                20                  25                  30

Thr Tyr Thr Gln Cys Thr Asp Gly Tyr Glu Trp Asp Pro Val Arg Gln
            35                  40                  45

Gln Cys Lys Asp Ile Asp Glu Cys Asp Ile Val Pro Asp Ala Cys Lys
        50                  55                  60
```

```
Gly Gly Met Lys Cys Val Asn His Tyr Gly Tyr Leu Cys Leu Pro
 65                  70                  75                  80

Lys Thr Ala Gln Ile Ile Val Asn Asn Glu Gln Pro Gln Gln Glu Thr
                 85                  90                  95

Gln Pro Ala Glu Gly Thr Ser Gly Ala Thr Thr Gly Val Val Ala Ala
                100                 105                 110

Ser Ser Met Ala Thr Ser Gly Val Leu Pro Gly Gly Phe Val Ala
                115                 120                 125

Ser Ala Ala Ala Val Ala Gly Pro Glu Met Gln Thr Gly Arg Asn Asn
                130                 135                 140

Phe Val Ile Arg Arg Asn Pro Ala Asp Pro Gln Arg Ile Pro Ser Asn
145                 150                 155                 160

Pro Ser His Arg Ile Gln Cys Ala Ala Gly Tyr Glu Gln Ser Glu His
                165                 170                 175

Asn Val Cys Gln Asp Ile Asp Glu Cys Thr Ala Gly Thr His Asn Cys
                180                 185                 190

Arg Ala Asp Gln Val Cys Ile Asn Leu Arg Gly Ser Phe Ala Cys Gln
                195                 200                 205

Cys Pro Pro Gly Tyr Gln Lys Arg Gly Asp Gln Cys Val Asp Ile Asp
                210                 215                 220

Glu Cys Thr Ile Pro Pro Tyr Cys His Gln Arg Cys Val Asn Thr Pro
225                 230                 235                 240

Gly Ser Phe Tyr Cys Gln Cys Ser Pro Gly Phe Gln Leu Ala Ala Asn
                245                 250                 255

Asn Tyr Thr Cys Val Asp Ile Asn Glu Cys Asp Ala Ser Asn Gln Cys
                260                 265                 270

Ala Gln Gln Cys Tyr Asn Ile Leu Gly Ser Phe Ile Cys Gln Cys Asn
                275                 280                 285

Gln Gly Tyr Glu Leu Ser Ser Asp Arg Leu Asn Cys Glu Asp Ile Asp
                290                 295                 300

Glu Cys Arg Thr Ser Ser Tyr Leu Cys Gln Tyr Gln Cys Val Asn Glu
305                 310                 315                 320

Pro Gly Lys Phe Ser Cys Met Cys Pro Gln Gly Tyr Gln Val Val Arg
                325                 330                 335

Ser Arg Thr Cys Gln Asp Ile Asn Glu Cys Glu Thr Thr Asn Glu Cys
                340                 345                 350

Arg Glu Asp Glu Met Cys Trp Asn Tyr His Gly Gly Phe Arg Cys Tyr
                355                 360                 365

Pro Arg Asn Pro Cys Gln Asp Pro Tyr Ile Leu Thr Pro Glu Asn Arg
                370                 375                 380

Cys Val
385

<210> SEQ ID NO 2
<211> LENGTH: 378
<212> TYPE: PRT
<213> ORGANISM: Artificial sequence
<220> FEATURE:
<223> OTHER INFORMATION: Point mutated Homo sapiens

<400> SEQUENCE: 2

Met Leu Lys Ala Leu Phe Leu Thr Met Leu Thr Leu Ala Leu Val Lys
 1               5                  10                  15

Ser Gln Asp Thr Glu Glu Thr Ile Thr Tyr Thr Gln Cys Thr Asp Gly
                20                  25                  30
```

Tyr Glu Trp Asp Pro Val Arg Gln Gln Cys Lys Asp Ile Asp Glu Cys
        35                  40                  45

Asp Ile Val Pro Asp Ala Cys Lys Gly Gly Met Lys Cys Val Asn His
 50                  55                  60

Tyr Gly Gly Tyr Leu Cys Leu Pro Lys Thr Ala Gln Ile Ile Val Asn
 65                  70                  75                  80

Asn Glu Gln Pro Gln Gln Glu Thr Gln Pro Ala Glu Gly Thr Ser Gly
                 85                  90                  95

Ala Thr Thr Gly Val Ala Ala Ser Ser Met Ala Thr Ser Gly Val
            100                 105                 110

Leu Pro Gly Gly Phe Val Ala Ser Ala Ala Val Ala Gly Pro
            115                 120                 125

Glu Met Gln Thr Gly Arg Asn Asn Phe Val Ile Arg Arg Asn Pro Ala
130                 135                 140

Asp Pro Gln Arg Ile Pro Ser Asn Pro Ser His Arg Ile Gln Cys Ala
145                 150                 155                 160

Ala Gly Tyr Glu Gln Ser Glu His Asn Val Cys Gln Asp Ile Asp Glu
                165                 170                 175

Cys Thr Ala Gly Thr His Asn Cys Arg Ala Asp Gln Val Cys Ile Asn
            180                 185                 190

Leu Arg Gly Ser Phe Ala Cys Gln Cys Pro Pro Gly Tyr Gln Lys Arg
            195                 200                 205

Gly Asp Gln Cys Val Asp Ile Asp Glu Cys Thr Ile Pro Pro Tyr Cys
210                 215                 220

His Gln Arg Cys Val Asn Thr Pro Gly Ser Phe Tyr Cys Gln Cys Ser
225                 230                 235                 240

Pro Gly Phe Gln Leu Ala Ala Asn Asn Tyr Thr Cys Val Asp Ile Asn
                245                 250                 255

Glu Cys Asp Ala Ser Asn Gln Cys Ala Gln Gln Cys Tyr Asn Ile Leu
            260                 265                 270

Gly Ser Phe Ile Cys Gln Cys Asn Gln Gly Tyr Glu Leu Ser Ser Asp
            275                 280                 285

Arg Leu Asn Cys Glu Asp Ile Asp Glu Cys Arg Thr Ser Ser Tyr Leu
            290                 295                 300

Cys Gln Tyr Gln Cys Val Asn Glu Pro Gly Lys Phe Ser Cys Met Cys
305                 310                 315                 320

Pro Gln Gly Tyr Gln Val Val Arg Ser Arg Thr Cys Gln Asp Ile Asn
                325                 330                 335

Glu Cys Glu Thr Thr Asn Glu Cys Arg Glu Asp Glu Met Cys Trp Asn
            340                 345                 350

Tyr His Gly Gly Phe Arg Cys Tyr Pro Arg Asn Pro Cys Gln Asp Pro
            355                 360                 365

Tyr Ile Leu Thr Pro Glu Asn Arg Cys Val
    370                 375

<210> SEQ ID NO 3
<211> LENGTH: 493
<212> TYPE: PRT
<213> ORGANISM: Artificial Sequence
<220> FEATURE:
<223> OTHER INFORMATION: Chemically Synthesized

<400> SEQUENCE: 3

Met Leu Lys Ala Leu Phe Leu Thr Met Leu Thr Leu Ala Leu Val Lys
 1               5                  10                  15

```
Ser Gln Asp Thr Glu Glu Thr Ile Thr Tyr Thr Gln Cys Thr Asp Gly
             20                  25                  30
Tyr Glu Trp Asp Pro Val Arg Gln Gln Cys Lys Asp Ile Asp Glu Cys
         35                  40                  45
Asp Ile Val Pro Asp Ala Cys Lys Gly Gly Met Lys Cys Val Asn His
 50                  55                  60
Tyr Gly Tyr Leu Cys Leu Pro Lys Thr Ala Gln Ile Ile Val Asn
 65              70                  75                  80
Asn Glu Gln Pro Gln Gln Glu Thr Gln Pro Ala Glu Gly Thr Ser Gly
                 85                  90                  95
Ala Thr Thr Gly Val Val Ala Ala Ser Ser Met Ala Thr Ser Gly Val
             100                 105                 110
Leu Pro Gly Gly Gly Phe Val Ala Ser Ala Ala Val Ala Gly Pro
         115                 120                 125
Glu Met Gln Thr Gly Arg Asn Asn Phe Val Ile Arg Arg Asn Pro Ala
 130                 135                 140
Asp Pro Gln Arg Ile Pro Ser Asn Pro Ser His Arg Ile Gln Cys Ala
 145                 150                 155                 160
Ala Gly Tyr Glu Gln Ser Glu His Asn Val Cys Gln Asp Ile Asp Glu
                 165                 170                 175
Cys Thr Ala Gly Thr His Asn Cys Arg Ala Asp Gln Val Cys Ile Asn
             180                 185                 190
Leu Arg Gly Ser Phe Ala Cys Gln Cys Pro Pro Gly Tyr Gln Lys Arg
         195                 200                 205
Gly Glu Gln Cys Val Asp Ile Asp Glu Cys Thr Ile Pro Pro Tyr Cys
 210                 215                 220
His Gln Arg Cys Val Asn Thr Pro Gly Ser Phe Tyr Cys Gln Cys Ser
 225                 230                 235                 240
Pro Gly Phe Gln Leu Ala Ala Asn Asn Tyr Thr Cys Val Asp Ile Asn
             245                 250                 255
Glu Cys Asp Ala Ser Asn Gln Cys Ala Gln Gln Cys Tyr Asn Ile Leu
         260                 265                 270
Gly Ser Phe Ile Cys Gln Cys Asn Gln Gly Tyr Glu Leu Ser Ser Asp
 275                 280                 285
Arg Leu Asn Cys Glu Asp Ile Asp Glu Cys Arg Thr Ser Ser Tyr Leu
 290                 295                 300
Cys Gln Tyr Gln Cys Val Asn Glu Pro Gly Lys Phe Ser Cys Met Cys
 305                 310                 315                 320
Pro Gln Gly Tyr Gln Val Val Arg Ser Arg Thr Cys Gln Asp Ile Asn
             325                 330                 335
Glu Cys Glu Thr Thr Asn Glu Cys Arg Glu Asp Glu Met Cys Trp Asn
         340                 345                 350
Tyr His Gly Gly Phe Arg Cys Tyr Pro Arg Asn Pro Cys Gln Asp Pro
 355                 360                 365
Tyr Ile Leu Thr Pro Glu Asn Arg Cys Val Cys Pro Val Ser Asn Ala
 370                 375                 380
Met Cys Arg Glu Leu Pro Gln Ser Ile Val Tyr Lys Tyr Met Ser Ile
 385                 390                 395                 400
Arg Ser Asp Arg Ser Val Pro Ser Asp Ile Phe Gln Ile Gln Ala Thr
             405                 410                 415
Thr Ile Tyr Ala Asn Thr Ile Asn Thr Phe Arg Ile Lys Ser Gly Asn
         420                 425                 430
```

```
Glu Asn Gly Glu Phe Tyr Leu Arg Gln Thr Ser Pro Val Ser Ala Met
                435                 440                 445

Leu Val Leu Val Lys Ser Leu Ser Gly Pro Arg Glu His Ile Val Asp
    450                 455                 460

Leu Glu Met Leu Thr Val Ser Ser Ile Gly Thr Phe Arg Thr Ser Ser
465                 470                 475                 480

Val Leu Arg Leu Thr Ile Ile Val Gly Pro Phe Ser Phe
                485                 490

<210> SEQ ID NO 4
<211> LENGTH: 443
<212> TYPE: PRT
<213> ORGANISM: Artificial Sequence
<220> FEATURE:
<223> OTHER INFORMATION: Chemically Synthesized

<400> SEQUENCE: 4

Met Leu Pro Cys Ala Ser Cys Leu Pro Gly Ser Leu Leu Leu Trp Ala
1               5                   10                  15

Leu Leu Leu Leu Leu Leu Gly Ser Ala Ser Pro Gln Asp Ser Glu Glu
                20                  25                  30

Pro Asp Ser Tyr Thr Glu Cys Thr Asp Gly Tyr Glu Trp Asp Pro Asp
            35                  40                  45

Ser Gln His Cys Arg Asp Val Asn Glu Cys Leu Thr Ile Pro Glu Ala
    50                  55                  60

Cys Lys Gly Glu Met Lys Cys Ile Asn His Tyr Gly Gly Tyr Leu Cys
65                  70                  75                  80

Leu Pro Arg Ser Ala Ala Val Ile Asn Asp Leu His Gly Glu Gly Pro
                85                  90                  95

Pro Pro Pro Val Pro Ala Gln His Pro Asn Pro Cys Pro Pro Pro Gly
            100                 105                 110

Tyr Glu Pro Asp Asp Gln Asp Ser Cys Val Asp Val Asp Glu Cys Ala
            115                 120                 125

Gln Ala Leu His Asp Cys Arg Pro Ser Gln Asp Cys His Asn Leu Pro
    130                 135                 140

Gly Ser Tyr Gln Cys Thr Cys Pro Asp Gly Tyr Arg Lys Ile Gly Pro
145                 150                 155                 160

Glu Cys Val Asp Ile Asp Glu Cys Arg Tyr Arg Tyr Cys Gln His Arg
                165                 170                 175

Cys Val Asn Leu Pro Gly Ser Phe Arg Cys Gln Cys Glu Pro Gly Phe
            180                 185                 190

Gln Leu Gly Pro Asn Asn Arg Ser Cys Val Asp Val Asn Glu Cys Asp
    195                 200                 205

Met Gly Ala Pro Cys Glu Gln Arg Cys Phe Asn Ser Tyr Gly Thr Phe
210                 215                 220

Leu Cys Arg Cys His Gln Gly Tyr Glu Leu His Arg Asp Gly Phe Ser
225                 230                 235                 240

Cys Ser Asp Ile Asp Glu Cys Ser Tyr Ser Ser Tyr Leu Cys Gln Tyr
                245                 250                 255

Arg Cys Val Asn Glu Pro Gly Arg Phe Ser Cys His Cys Pro Gln Gly
            260                 265                 270

Tyr Gln Leu Leu Ala Thr Arg Leu Cys Gln Asp Ile Asp Glu Cys Glu
    275                 280                 285

Ser Gly Ala His Gln Cys Ser Glu Ala Gln Thr Cys Val Asn Phe His
290                 295                 300
```

```
Gly Gly Tyr Arg Cys Val Asp Thr Asn Arg Cys Val Glu Pro Tyr Ile
305                 310                 315                 320

Gln Val Ser Glu Asn Arg Cys Leu Cys Pro Ala Ser Asn Pro Leu Cys
            325                 330                 335

Arg Glu Gln Pro Ser Ser Ile Val His Arg Tyr Met Thr Ile Thr Ser
            340                 345                 350

Glu Arg Ser Val Pro Ala Asp Val Phe Gln Ile Gln Ala Thr Ser Val
        355                 360                 365

Tyr Pro Gly Ala Tyr Asn Ala Phe Gln Ile Arg Ala Gly Asn Ser Gln
        370                 375                 380

Gly Asp Phe Tyr Ile Arg Gln Ile Asn Asn Val Ser Ala Met Leu Val
385                 390                 395                 400

Leu Ala Arg Pro Val Thr Gly Pro Arg Glu Tyr Val Leu Asp Leu Glu
                405                 410                 415

Met Val Thr Met Asn Ser Leu Met Ser Tyr Arg Ala Ser Ser Val Leu
            420                 425                 430

Arg Leu Thr Val Phe Val Gly Ala Tyr Thr Phe
            435                 440
```

<210> SEQ ID NO 5
<211> LENGTH: 448
<212> TYPE: PRT
<213> ORGANISM: Artificial Sequence
<220> FEATURE:
<223> OTHER INFORMATION: Chemically Synthesized

<400> SEQUENCE: 5

```
Met Pro Gly Ile Lys Arg Ile Leu Thr Val Thr Ile Leu Ala Leu Cys
1               5                   10                  15

Leu Pro Ser Pro Gly Asn Ala Gln Ala Gln Cys Thr Asn Gly Phe Asp
            20                  25                  30

Leu Asp Arg Gln Ser Gly Gln Cys Leu Asp Ile Asp Glu Cys Arg Thr
        35                  40                  45

Ile Pro Glu Ala Cys Arg Gly Asp Met Met Cys Val Asn Gln Asn Gly
    50                  55                  60

Gly Tyr Leu Cys Ile Pro Arg Thr Asn Pro Val Tyr Arg Gly Pro Tyr
65                  70                  75                  80

Ser Asn Pro Tyr Ser Thr Pro Tyr Ser Gly Pro Tyr Pro Ala Ala Ala
            85                  90                  95

Pro Pro Leu Ser Ala Pro Asn Tyr Pro Thr Ile Ser Arg Pro Leu Ile
            100                 105                 110

Cys Arg Phe Gly Tyr Gln Met Asp Glu Ser Asn Gln Cys Val Asp Val
        115                 120                 125

Asp Glu Cys Ala Thr Asp Ser His Gln Cys Asn Pro Thr Gln Ile Cys
    130                 135                 140

Ile Asn Thr Glu Gly Gly Tyr Thr Cys Ser Cys Thr Asp Gly Tyr Trp
145                 150                 155                 160

Leu Leu Glu Gly Gln Cys Leu Asp Ile Asp Glu Cys Arg Tyr Gly Tyr
            165                 170                 175

Cys Gln Gln Leu Cys Ala Asn Val Pro Gly Ser Tyr Ser Cys Thr Cys
        180                 185                 190

Asn Pro Gly Phe Thr Leu Asn Glu Asp Gly Arg Ser Cys Gln Asp Val
    195                 200                 205

Asn Glu Cys Ala Thr Glu Asn Pro Cys Val Gln Thr Cys Val Asn Thr
    210                 215                 220
```

Tyr Gly Ser Phe Ile Cys Arg Cys Asp Pro Gly Tyr Glu Leu Glu
225                 230                 235                 240

Asp Gly Val His Cys Ser Asp Met Asp Glu Cys Ser Phe Ser Glu Phe
                245                 250                 255

Leu Cys Gln His Glu Cys Val Asn Gln Pro Gly Thr Tyr Phe Cys Ser
                260                 265                 270

Cys Pro Pro Gly Tyr Ile Leu Leu Asp Asp Asn Arg Ser Cys Gln Asp
                275                 280                 285

Ile Asn Glu Cys Glu His Arg Asn His Thr Cys Asn Leu Gln Gln Thr
                290                 295                 300

Cys Tyr Asn Leu Gln Gly Gly Phe Lys Cys Ile Asp Pro Ile Arg Cys
305                 310                 315                 320

Glu Glu Pro Tyr Leu Arg Ile Ser Asp Asn Arg Cys Met Cys Pro Ala
                325                 330                 335

Glu Asn Pro Gly Cys Arg Asp Gln Pro Phe Thr Ile Leu Tyr Arg Asp
                340                 345                 350

Met Asp Val Val Ser Gly Arg Ser Val Pro Ala Asp Ile Phe Gln Met
                355                 360                 365

Gln Ala Thr Thr Arg Tyr Pro Gly Ala Tyr Tyr Ile Phe Gln Ile Lys
                370                 375                 380

Ser Gly Asn Glu Gly Arg Glu Phe Tyr Met Arg Gln Thr Gly Pro Ile
385                 390                 395                 400

Ser Ala Thr Leu Val Met Thr Arg Pro Ile Lys Gly Pro Arg Glu Ile
                405                 410                 415

Gln Leu Asp Leu Glu Met Ile Thr Val Asn Thr Val Asn Phe Arg
                420                 425                 430

Gly Ser Ser Val Ile Arg Leu Arg Ile Tyr Val Ser Gln Tyr Pro Phe
                435                 440                 445

<210> SEQ ID NO 6
<211> LENGTH: 60
<212> TYPE: PRT
<213> ORGANISM: Homo sapiens

<400> SEQUENCE: 6

Gln Gln Glu Thr Gln Pro Ala Glu Gly Thr Ser Gly Ala Thr Thr Gly
1               5                   10                  15

Val Val Ala Ala Ser Ser Met Ala Thr Ser Gly Val Leu Pro Gly Gly
                20                  25                  30

Gly Phe Val Ala Ser Ala Ala Val Ala Gly Pro Glu Met Gln Thr
                35                  40                  45

Gly Arg Asn Asn Phe Val Ile Arg Arg Asn Pro Ala
        50                  55                  60

<210> SEQ ID NO 7
<211> LENGTH: 38
<212> TYPE: PRT
<213> ORGANISM: Mus musculus

<400> SEQUENCE: 7

Met Ala Thr Ser Gly Val Val Pro Gly Gly Gly Phe Met Ala Ser Ala
1               5                   10                  15

Thr Ala Val Ala Gly Pro Glu Val Gln Thr Gly Arg Asn Asn Phe Val
                20                  25                  30

Ile Arg Arg Asn Pro Ala
        35

<210> SEQ ID NO 8
<211> LENGTH: 38
<212> TYPE: PRT
<213> ORGANISM: Rattus norvegicus

<400> SEQUENCE: 8

Met Ala Thr Ser Gly Val Ile Pro Gly Gly Phe Ile Ala Ser Ala
1               5                   10                  15

Thr Ala Val Ala Gly Pro Glu Val Gln Thr Gly Arg Asn Asn Phe Val
                20                  25                  30

Ile Arg Arg Asn Pro Ala
            35

<210> SEQ ID NO 9
<211> LENGTH: 68
<212> TYPE: PRT
<213> ORGANISM: Homo sapiens

<400> SEQUENCE: 9

Thr Thr Tyr Gln Met Asp Val Asn Pro Glu Gly Lys Tyr Ser Phe Gly
1               5                   10                  15

Ala Thr Cys Val Lys Lys Cys Pro Arg Asn Tyr Val Val Thr Asp His
                20                  25                  30

Gly Ser Cys Val Arg Ala Cys Gly Ala Asp Ser Tyr Glu Met Glu Glu
            35                  40                  45

Asp Gly Val Arg Lys Cys Lys Lys Cys Glu Gly Pro Cys Arg Lys Val
        50                  55                  60

Cys Asn Gly Ile
65

<210> SEQ ID NO 10
<211> LENGTH: 68
<212> TYPE: PRT
<213> ORGANISM: Homo sapiens

<400> SEQUENCE: 10

Thr Thr Tyr Gln Met Asp Val Asn Pro Glu Gly Lys Tyr Ser Phe Gly
1               5                   10                  15

Ala Thr Cys Val Lys Lys Cys Pro Arg Asn Tyr Val Val Thr Asp His
                20                  25                  30

Gly Ser Cys Val Arg Ala Cys Gly Ala Asp Ser Tyr Glu Met Glu Glu
            35                  40                  45

Asp Gly Val Arg Lys Cys Lys Lys Cys Glu Gly Pro Cys Arg Lys Val
        50                  55                  60

Cys Asn Gly Ile
65

<210> SEQ ID NO 11
<211> LENGTH: 68
<212> TYPE: PRT
<213> ORGANISM: Homo sapiens

<400> SEQUENCE: 11

Thr Thr Tyr Gln Met Asp Val Asn Pro Glu Gly Lys Tyr Ser Phe Gly
1               5                   10                  15

Ala Thr Cys Val Lys Lys Cys Pro Arg Asn Tyr Val Val Thr Asp His
                20                  25                  30

Gly Ser Cys Val Arg Ala Cys Gly Ala Asp Ser Tyr Glu Met Glu Glu
            35                  40                  45

```
Asp Gly Val Arg Lys Cys Lys Lys Cys Glu Gly Pro Cys Arg Lys Val
         50                  55                  60

Cys Asn Gly Ile
 65

<210> SEQ ID NO 12
<211> LENGTH: 68
<212> TYPE: PRT
<213> ORGANISM: Homo sapiens

<400> SEQUENCE: 12

Thr Thr Tyr Gln Met Asp Val Asn Pro Glu Gly Lys Tyr Ser Phe Gly
 1               5                  10                  15

Ala Thr Cys Val Lys Lys Cys Pro Arg Asn Tyr Val Val Thr Asp His
             20                  25                  30

Gly Ser Cys Val Arg Ala Cys Gly Ala Asp Ser Tyr Glu Met Glu Glu
         35                  40                  45

Asp Gly Val Arg Lys Cys Lys Lys Cys Glu Gly Pro Cys Arg Lys Val
         50                  55                  60

Cys Asn Gly Ile
 65

<210> SEQ ID NO 13
<211> LENGTH: 45
<212> TYPE: PRT
<213> ORGANISM: Homo sapiens

<400> SEQUENCE: 13

Lys Gly Asn Tyr Val Val Thr Asp His Gly Ser Cys Val Arg Ala Cys
 1               5                  10                  15

Gly Ala Asp Ser Tyr Glu Met Glu Glu Asp Gly Val Arg Lys Cys Lys
             20                  25                  30

Lys Cys Glu Gly Pro Cys Arg Lys Val Cys Asn Gly Ile
         35                  40                  45
```

FIBULIN PROTEIN VARIANTS AND CORRESPONDING NUCLEIC ACID SEQUENCES

The present application claims the benefit of International Patent Application PCT US201432597, filed on Apr. 1, 2014 and U.S. Provisional Patent Application Ser. No. 61/807,445, filed on Apr. 2, 2013, each of which are hereby incorporated by reference in its entirety.

FIELD OF THE INVENTIONS

Embodiments of the invention relate to fibulin 3 (also referred to as EGF-containing fibulin-like extracellular matrix protein 1 (EFEMP1)) polypeptide variants, and nucleotide sequences that code for them, characterized by having one or more activities of inhibiting cancer growth, inhibiting cancer cell invasion, and inhibiting cancer recurrence.

BACKGROUND OF THE INVENTIONS

Fibulins are a seven-member family of secreted glycoproteins characterized by possessing repeated epidermal growth-factor-like domains and a unique C-terminal structure. Studies of fibulin protein function in cancer indicate that some fibulin proteins have tumor-suppressor activity and some have oncogenic activity. Moreover, some individual fibulin proteins (e.g., fibulin 3/EFEMP1) demonstrate tumor suppressor activity or oncogenic activity in a tissue-specific manner.

EFEMP1 tumor suppressor function is indicated by the following. EFEMP1 has an anti-angiogenic function via suppression of endothelial cell sprouting. EFEMP1 overexpression inhibits tumorigenicity of fibrosarcoma cells. Reduced EFEMP1 expression and/or EFEMP1 promoter methylation occurs in lung, liver, breast, colon, prostate, and nasopharyngeal carcinoma. EFEMP1 expression in glioblastoma multiforme, hepatocellular, and nasopharyngeal carcinoma is correlated with a favorable prognosis. EFEMP1 suppresses AKT signaling activity in nasopharyngeal carcinoma and glioblastoma cell lines EFEMP1 oncogenic function is indicated by the following. Elevated EFEMP1 expression has been correlated to poor prognosis for cervical cancer. The results of a clinical trial demonstrated that EFEMP1 over-expression was correlated to poor prognosis for breast carcinoma. In pancreatic adenocarcinoma cells, EFEMP1 over-expression promotes xenograft formation. EFEMP1 activates AKT signaling activity in pancreatic carcinoma cell lines. In certain glioma cells, EFEMP1 has been shown to enhance in vitro substrate-specific cell adhesion and promote cell motility and dispersion.

The deadly form of brain cancer, glioblastoma multiforme (GBM), for which there is not yet any effective treatment, is made up of disparate subpopulations of cells characterized by having distinct proliferation and infiltration properties. The mechanism underlying GBM recurrence after treatment, such as surgery, radiation, and chemotherapy, has not been conclusively identified. It has been speculated that recurrence is caused by an infiltrative subpopulation of GBM cells that have neural stem cell properties (so-called tumor stem cells) and are resistant to radiation and chemotherapy. GBM growth appears largely dependent on an angiogenic tumor microenvironment, and anti-angiogenic therapies have been shown to temporarily repress GBM tumor growth. But anti-angiogenic therapies do not improve overall survival of GBM patients and result in tumor recurrence with an increased pattern of infiltration. Previously, a therapy targeting glioma cell infiltration has been lacking.

SUMMARY OF THE INVENTIONS

In the past 30 years, only a modest 2.5 month median survival increase has been achieved for GBM cancer patients by adding concomitant temozolamide treatment to radiotherapy after surgery. An object of the present invention is to provide cancer therapies that can provide inhibition of cancer cell growth, infiltration, and/or recurrence in cancers, such as GBM. Accordingly, embodiments of the invention provide amino acid sequence variants of wild type EFEMP1 protein characterized by modulating, in cancer cells, the activity and/or expression level of proteins that include EGFR, AKT, protein tyrosine kinase 2 (PTK2), and NOTCH. The cancer can be a low-medium grade glioma, a high grade glioma, such as GBM, a fibrosarcoma, a colorectal cancer, a lung cancer, a colon cancer, a liver cancer, a breast cancer, a prostate cancer, or a nasopharyngeal cancer. And the cancer cell can be a cancer stem cell and non-stem-like cancer cell.

Certain embodiments of the invention provide polypeptides that: (i) comprise an amino acid sequence that shares at least about 70%, about 75%, about 80%, about 85%, about 90%, about 95%, about 97%, about 99%, or 100% identity with the amino acid sequence set forth in SEQ ID NO 1 or SEQ ID NO 2; and (ii) possess at least one activity selected from the group consisting of an inhibition of cancer cell invasion, an inhibition of tumor growth, and an inhibition of cancer recurrence. Some embodiments of the invention provide nucleic acid molecules that comprise a nucleotide sequence that encode for such polypeptides.

Certain embodiments of the invention provide polypeptides that: (i) comprise an amino acid sequence that shares at least about 85%, about 90%, about 95%, about 97%, about 99%, or 100% identity with the amino acid sequence set forth in SEQ ID NO 1 or SEQ ID NO 2, and (ii) possess at least one activity selected from the group consisting of an inhibition of EGFR expression, an inhibition of EGFR activity, an inhibition of AKT expression, an inhibition of AKT activity, an inhibition of PKT2 expression, an inhibition of PKT2 activity, an inhibition of NOTCH expression, and an inhibition of NOTCH activity. Some embodiments of the invention provide nucleic acid molecules that comprise a nucleotide sequence that encode for such polypeptides.

BRIEF DESCRIPTION OF THE DRAWINGS

FIG. 1A is a CLUSTAL W amino acid sequence alignment of fibulin proteins EFEMP1, EFEMP2, and fibulin 5 (FBLN5). FIG. 1B is a CLUSTAL W amino acid sequence alignment of an EGFR-homologous region (EHR) in human, mouse, and rat EFEMP1 protein, four isoforms of human EGFR protein, and a deletion mutant of EGFR.

DETAILED DESCRIPTION OF THE INVENTIONS

An object achieved by the present invention is to provide amino acid sequences of EFEMP1 polypeptide variants that possess at least one activity of inhibiting cancer growth, inhibiting cancer cell infiltration, and inhibiting cancer recurrence, such as a glioma (e.g., a glioblastoma multiforme). In some embodiments, amino acid sequence variants of wild-type EFEMP1 protein, at times referred to as EFEMP1 derived tumor suppressor proteins (ETSP), inhibit proliferation and invasion activities of fast proliferative and invasive glioma tumor cell subpopulations separately and together in orthotopic tumor formatting. Such ETSPs have been discovered, at least in part, by amino acid sequence homology studies of wild-type EFEMP1 and experimentation with variant EFEMP1 polypeptides.

FIG. 1A is a CLUSTAL W (1.83) alignment of the amino acid sequences of wild-type EFEMP1, EFEMP2, and fibulin 5 (FBLN5) which shows that, although EFEMP1 is a longer protein than EFEMP2 and FBLN5, a high degree of sequence similarity exists among those proteins. FIG. 1A also shows the location of weak (RGE) and strong (RGD) integrin binding sites in wild-type EFEMP1 and FBLN5, respectively. FIG. 1B is a CLUSTAL W (1.83) alignment of a 38 amino acid EGFR-homologous region (EHR) in EFEMP1. The aligned EHR amino acid sequences are: human, mouse, and rat EFEMP1; four isoforms of human EGFR (EGFRv1, EGFRv2, EGFRv3, EGFRv4); and a deletion mutant of EGFR (EGFRvIII) identified in human cancers.

Figure 2:
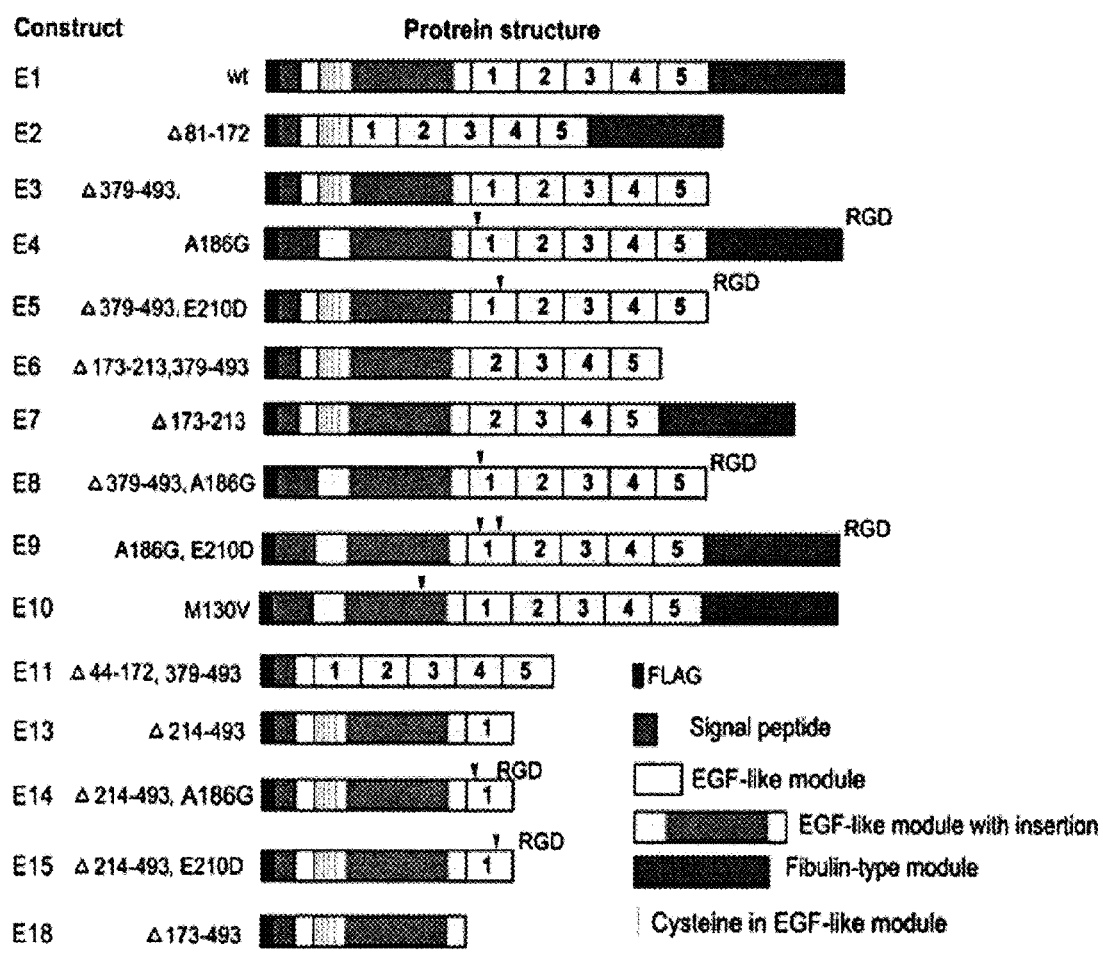
FIG. 2 is a schematic of the modular structure of a FLAG-tagged, wild-type EFEMP1 protein construct E1 and a panel of FLAG-tagged, EFEMP1 protein variant constructs E2-E11, E13-E15, and E18.

FIG. 2 is a schematic of modular domains present in a panel of FLAG-tagged, EFEMP1 proteins encoded by constructs E1-E11, E13-E15, and E18. Construct E1 encodes a full-length EFEMP1 protein having wild-type (wt) amino acid sequence, which includes a signal peptide, a DSL motif, an EGF-like module with an insertion, five EGF-like modules numbered 1-5, and a fibulin-type module.

Construct E2 encodes an EFEMP1 variant in which amino acids 81-172 have been deleted, largely eliminating the EFEMP1-specific, EGF-like module with an insertion of wt EFEMP1.

Construct E3 encodes an EFEMP1 variant in which amino acids 379-493 have been deleted, largely eliminating the fibulin-type module of wt EFEMP1.

Construct E4 encodes an EFEMP1 variant in which amino acid 186 has been changed from Alanine to Glycine, which converts a weak integrin binding site of wt EFEMP1 into a strong integrin binding site.

Construct E5 encodes an EFEMP1 variant in which amino acids 379-493 have been deleted, largely eliminating the fibulin-type module of wt EFEMP1, and in which amino acid 210 has been changed from glutamic acid to aspartic acid, converting a weak integrin binding site of wt EFEMP1 into a strong integrin binding site.

Construct E6 encodes an EFEMP1 variant in which amino acids 173-213 and 379-493 have been deleted, largely eliminating the EGF-like module 1 and the fibulin-type module of wt EFEMP1.

Construct E7 encodes an EFEMP1 variant in which amino acids 173-213 have been deleted, largely eliminating EGF-like module 1 of wt EFEMP1.

Construct E8 encodes an EFEMP1 variant in which amino acids 379-493 have been deleted, largely eliminating the fibulin-type module of wt EFEMP1, and in which amino acid 186 has been changed from Alanine to Glycine, which converts a weak integrin binding site of wt EFEMP1 into a strong integrin binding site.

Construct E9 encodes an EFEMP1 variant in which amino acid 186 has been changed from Alanine to Glycine, amino acid 210 has been changed from glutamic acid to aspartic acid, converting two weak integrin binding sites of wt EFEMP1 into two strong integrin binding sites.

Construct E10 encodes an EFEMP1 variant in which amino acid 130 has been changed from Methionine to Valine, converting that amino acid residue in human wt EFEMP1, positioned in a 20 amino acid sequence in the EGF-like module with insertion that shares sequence similarity to EGFR, to the corresponding mouse and rat EFEMP1 residue.

Construct E11 encodes an EFEMP1 variant in which amino acids 44-172 and 379-493 have been deleted, partly eliminating the DSL motif of wt EFEMP1 and largely eliminating the EGF-like module with insertion and the fibulin-type module of wt EFEMP1.

Construct E13 encodes an EFEMP1 variant in which amino acids 214-493 have been deleted, largely eliminating the EGF-like modules 2-5 and the fibulin-type module of wt EFEMP1.

Construct E14 encodes an EFEMP1 variant in which amino acids 214-493 have been deleted, largely eliminating EGF-like modules 2-5 and the fibulin-type module of wt EFEMP1, and in which amino acid 186 has been changed from Alanine to Glycine, converting a weak integrin binding site of wt EFEMP1 into a strong one.

Construct E15 encodes an EFEMP1 variant in which amino acids 214-493 have been deleted, largely eliminating EGF-like modules 2-5 and the fibulin-type module of wt EFEMP1, and in which amino acid 210 has been changed from Glutamic Acid to Aspartic Acid, converting a weak integrin binding site of wt EFEMP1 into a strong one.

Construct E18 encodes an EFEMP1 variant in which amino acids 173-493 have been deleted, largely eliminating EGF-like modules 1-5 and the fibulin-type module of wt EFEMP1.

U251 is a high-tumorigenicity malignant glioma cell line derived from human glioblastoma multiforme. Different protocols exist for culturing U251. Parental culture of U251 is serum-containing and adherent. Neural sphere (NS) culture of U251 is serum-free and non-adherent, or fibronectin-anchored adherent, with supplements used for culture of normal neural stem cells. U251 is composed of disparate subpopulations of cells. In parental culture, the majority cell subpopulation carries two normal copies of chromosome 7 and one 7q-deleted copy of chromosome 7. In NS culture, the majority cell subpopulation carries one normal copy of chromosome 7 and one 7q-deleted copy of chromosome 7.

U251 cells that carry two normal copies of chromosome 7 and one 7q-deleted copy of chromosome 7 show fast proliferation in the S.C. xenograft assay described in Example 4. They also are also lacking in invasiveness, but form the bulk of the tumor mass, in the I.C. xenograft assay described in Example 8.

U251-NS cells that carry one normal copy of chromosome 7 and one 7q-deleted copy of chromosome 7 show high levels of invasiveness in the matrigel invasion and zymography assays described in Examples 5 and 6. They also possess tumor stem-like cell features and are lacking in tumorigenicity in the S.C. xenograft assay described in Example 4. U251-NS cells transfected to overexpress vascular endothelial growth factor form tumors in subcutaneous (S.C.) xenograft assay described in Example 4. U251-NS cells forms highly invasive tumor in intracranial (I.C.) xenograft assay described in Example 8. And they are more invasive than U251 cells that carry two normal copies of chromosome 7 and one 7q-deleted copy of chromosome 7 in the IC xenograft assay described in Example 8.

Table 1 reports qRT-PCR results obtained with three types of U251 cell cultures. The first type was parental culture of U251 cell lines stably transfected with the E1, E2, E3, E4, E5, E6, E7, E8, E9, E10, E11, E13, E14, E15 and E18 pcDNA 3.1+ constructs described in FIG. 2 and Example 1 and with plasmid vector pcDNA 3.1+ (Vec). The second type was parental culture of U251 cells infected with the E1, E2, E5, E6, E7, E8, E11, E13, E15, and E18 pTRIPZ lentiviral constructs described in FIG. 2 and Example 2 and with plasmid vector pTRIPZ (Vec). The third type was neural sphere culture of U251 (U251-NS) cells infected with the E1, E2, E3, E5, E7, E8, E10, E11, E13, E15, and E18 pTRIPZ lentiviral constructs described in FIG. 2 and Example 2 and with plasmid vector pTRIPZ (Vec). The forward primer of the PCR primer pair annealed to the FLAG tag and the reverse primer annealed to exon 4 of EFEMP1. The results of Table 1 indicate that the E1, E2, E3, E4, E5, E6, E7, E8, E9, E10, E11, E13, E14, E15 and E18 constructs are expressed in parental cultures of U251 transfectant cells. The results of Table 1 also indicate that the E1, E2, E5, E6, E7, E8, E11, E13, E15, and E18 constructs are expressed in parental cultures of U251 lentiviral infectant cells, in a doxycycline-inducible manner. Also that the E1, E2, E3, E5, E7, E8, E10, E11, E13, E15, and E18 constructs are expressed in doxycycline containing neural sphere cultures of U251 (U251-NS) lentiviral infectant cells.

TABLE 1

FLAG-EFEMP1/ACTB *1000

| | Cell | | | |
|---|---|---|---|---|
| | U251 pcDNA | U251 pTRPZ lentiviral infectant | | U251-NS |
| Construct | transfectant | (−) Dox | (+) Dox | (+) Dox |
| Vector | | 0.0 | 0.0 | 0.1 |
| E1 | 1.6 | 0.1 | 12.7 | 133.3 |
| E2 | 23.7 | 0.1 | 3.4 | 74.2 |
| E3 | 81.0 | NE | N/E | 46.7 |
| E5 | 22.4 | 0.1 | 4.5 | 1.9 |
| E6 | 29.6 | 0.1 | 8.1 | |
| E7 | 1.8 | 0.0 | 3.3 | 43.8 |
| E8 | 1.6 | 0.1 | 5.2 | 14.2 |
| E9 | 1.4 | N/E | N/E | N/E |
| E10 | 49.5 | N/E | N/E | 55.2 |
| E11 | 153.9 | 0.1 | 54.9 | 198.0 |
| E13 | 24.2 | 0.1 | 25.4 | 6.6 |
| E15 | 62.5 | 0.1 | 9.3 | 85.4 |
| E18 | N/E | 0.2 | 6.9 | 142.3 |

N/E: Not examined

Table 2 reports results obtained with the anchorage-independent growth and cell proliferation soft agar colony formation assay described in Example 3, initiated with parental cultures of U251 cell lines stably transfected with the E1, E2, E3, E4, E5, E6, E7, E8, E9, E10, E11, E13, E14, and E15 pcDNA 3.1+ constructs described in FIG. 2 and Example 1 and with plasmid vector pcDNA 3.1+ (Vec). Table 2 also reports results obtained with the anchorage-independent growth and cell proliferation soft agar colony formation assay described in Example 3, initiated with neural sphere cultures of U251 cells (U251-NS) infected with the E1, E2, E5, E7, E8, E10, E11, E13, E15, and E18 pTRIPZ lentiviral constructs described in FIG. 2 and Example 2 and with plasmid vector pTRIPZ (Vec). Lentivial infectants were cultured in medium containing doxycycline to induce transgene expression, and expression was verified by assaying RFP expression with a fluorescent microscope. The results of Table 2 indicate that EFEMP1 protein variants expressed from constructs E2, E5, E6, E7, E8, E11, E13, E14, and E15 suppress U251 and/or U251-NS cell growth. They also indicate that EFEMP1 protein variant E3 increased cell proliferation in the U251 soft agar assay.

TABLE 2

| | U251 | | U251-NS | |
|---|---|---|---|---|
| Construct | Size | Number (Ave, SD) | Size | Number (Ave, SD) |
| Vec | 3+ | 1.0, 0.3 | 2+ | 1.0, 0.1 |
| E1 | 3+ | 1.1, 0.4 | 1+ | 0.6, 0.2 |
| E2 ✓ | 3+ | 0.6, 0.2 | 1+ | 1.4, 0.2 |
| E3 | 6+ | 0.7, 0.1 | | |
| E4 | 3+ | 1.0, 0.2 | | |
| E5 ✓ | 3+ | 1.1, 0.4 | 1+ | 0.5, 0.1 |
| E6 ✓ | 1+ | 0.2, 0.1 | | |
| E7 ✓ | 1+ | 0.7, 0.3 | 1+ | 0.5, 0.2 |
| E8 ✓ | 3+ | 1.3, 0.4 | 1+ | 0.6, 0.1 |
| E9 | 3+ | 1.1, 0.1 | | |
| E10 | 4+ | 0.7, 0.1 | 2+ | 1.0, 0.2 |
| E11 ✓ | 1+ | 0.3, 0.1 | 1+ | 0.8, 0.2 |
| E13 ✓ | 3+ | 1.6, 0.2 | 1+ | 0.7, 0.2 |
| E14 ✓ | 3+ | 0.6, 0.2 | | |
| E15 ✓ | 3+ | 0.5, 0.1 | 1+ | 1.7, 0.3 |
| E18 | | | 2+ | 1.5, 0.2 |

Figure 3A:
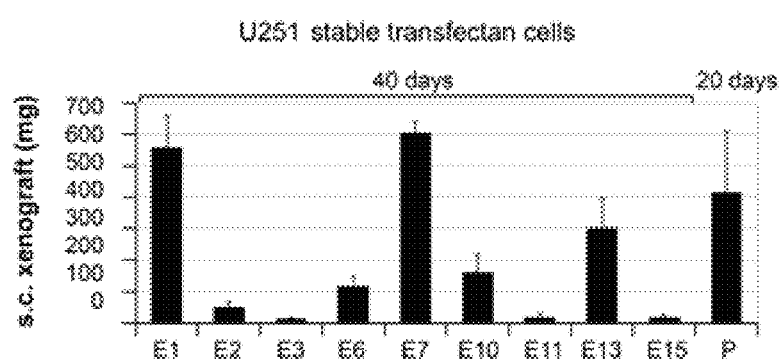
FIG. 3A is a plot of tumor weights from the S.C. xenograft assay described in Example 4, initiated with parental cultures of U251 cell lines stably transfected with the E1-E3, E6-E7, E10-E11, E13, and E15 pcDNA 3.1+ constructs described in FIG. 2 and Example 1 and vector pcDNA 3.1+ (P).

FIG. 3A is a plot of tumor weights from the S.C. xenograft assay described in Example 4, initiated with parental cultures of U251 cell lines stably transfected with the E1, E2, E3, E6, E7, E10, E11, E13, and E15 pcDNA 3.1+ constructs described in FIG. 2 and Example 1 and with U251 parental control cells (P). The results indicate that the EFEMP1 protein variants expressed from constructs E2, E3, E5, E6, E11, and E15 suppress U251 cells forming tumors in the S.C. xenograft assay.

Figure 3B:
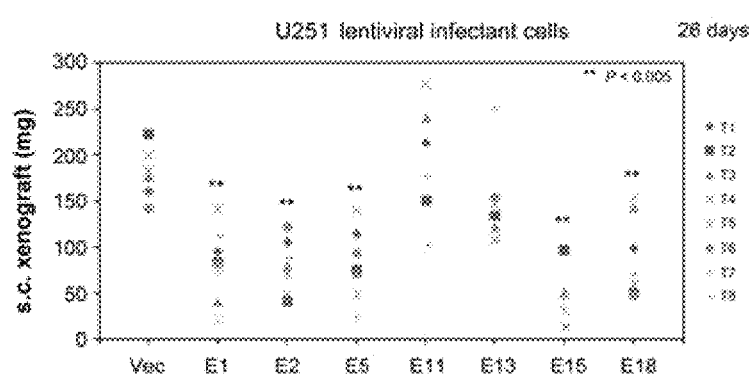
FIG. 3B is a plot of tumor weights from the S.C. xenograft assay described in Example 4, initiated with parental cultures of U251 cells infected with the E1, E2, E5, E11, E13, E15, and E18 pTRIPZ lentiviral constructs described in FIG. 2 and Example 1 and vector pTRIPZ (Vec).

FIG. 3B is a plot of tumor weights from the S.C. xenograft assay described in Example 4, initiated with parental cultures of U251 cells infected with the E1, E2, E5, E11, E13, E15, and E18 pTRIPZ lentiviral constructs described in FIG. 2 and Example 2 and with plasmid vector pTRIPZ (Vec). Mice were fed with doxycycline-containing water from day 1 and throughout the experiment. RFP-expression was shown in the resulting tumors. The results indicate that the EFEMP1 protein variants expressed from constructs E2, E5, E15, and E18 suppress U251 cells forming tumors in the S.C. xenograft assay.

Figure 4A:
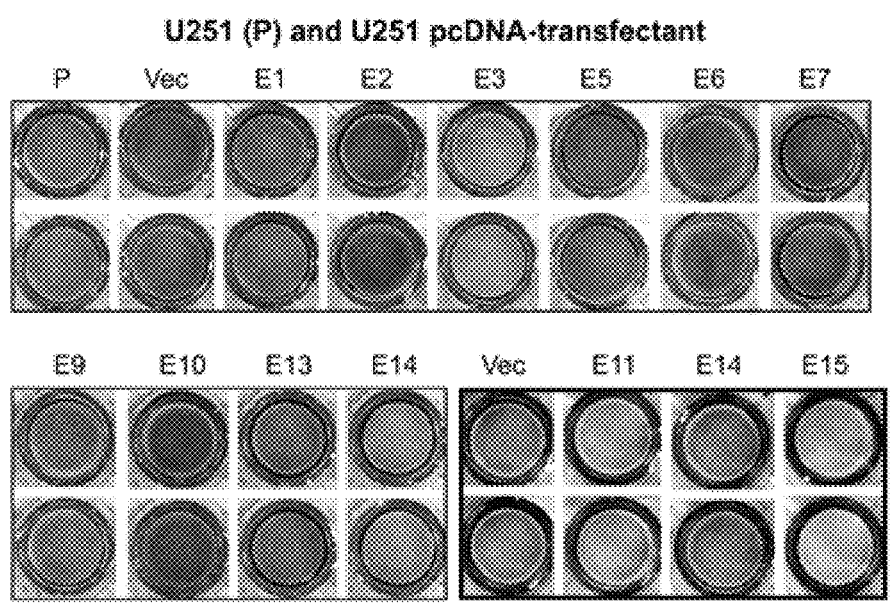
FIG. 4A is a photograph of the bottom surface of transwell inserts from the matrigel cell invasion assay described in Example 5, initiated with parental cultures of U251 cell lines stably transfected with the E1-E3, E5, E6-E7, E9-E10, E11, and E13-E15 pcDNA 3.1+ constructs described in FIG. 2 and Example 1; vector pcDNA 3.1+ (Vec); and U251 parental control cells (P).

FIG. 4A is a photograph of cell plates from the matrigel cell invasion assay described in Example 5, initiated with parental cultures of U251 cell lines stably transfected with the E1, E2, E3, E5, E6, E7, E9, E10, E11, E13, E14, and E15 pcDNA 3.1+ constructs described in FIG. 2 and Example 1 and with plasmid vector pcDNA 3.1+ (Vec) and with U251 parental control cells (P). The results indicate that the EFEMP1 protein variants expressed from constructs E3, E11, and E15 suppress the invasiveness of U251 cells in the matrigel assay.

Figure 4B:
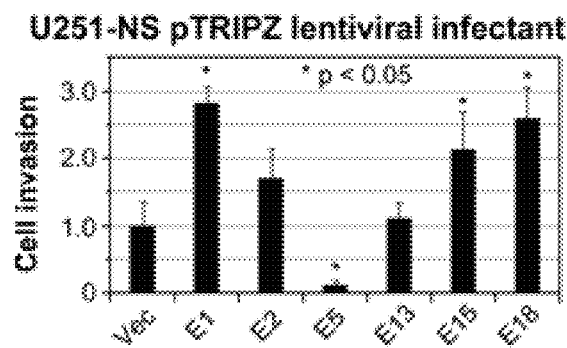
FIG. 4B is a plot of cell invasion from the matrigel invasion assay described in Example 5, initiated with neural sphere cultures of U251 cells infected with the E1, E2, E5, 13, E15, and E18 pTRIPZ lentiviral constructs described in FIG. 2 and Example 1 and vector pTRIPZ (Vec).

FIG. 4B is a plot of cell invasion in the matrigel invasion assay described in Example 5, initiated with neural sphere cultures of U251 (U251-NS) cells infected with the E1, E2, E5, E13, E15, and E18 pTRIPZ lentiviral constructs described in FIG. 2 and Example 2 and with plasmid vector pTRIPZ (Vec). Lentiviral infectants were cultured in medium containing doxycycline to induce transgene expression, and expression was verified by assaying RFP expression with a fluorescent microscope. The results indicate that the EFEMP1 protein variant expressed from construct E5 significantly inhibits U251-NS cell invasion; whereas the wild-type EFEMP1 and EFEMP1 protein variants expressed from constructs E1, E15, and E18 significantly promote U251-NS cell invasion.

Figure 4C:
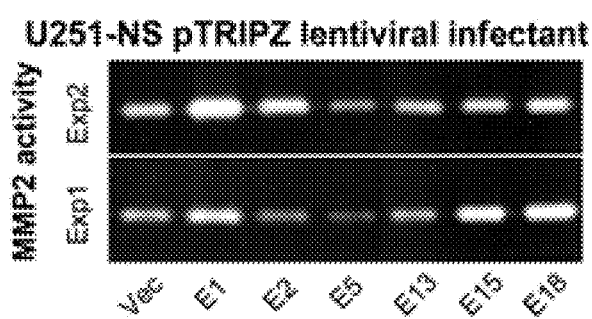
FIG. 4C is a photograph of gels of the zymography assay described in Example 6, conducted with cells of the matrigel invasion assays pictured in FIG. 4B.

FIG. 4C is a photograph of two gels of the zymography assay described in Example 6, conducted with cells from the matrigel invasion assay pictured in FIG. 4B. The results indicate that U251-NS glioma cells secrete active MMP2 (~67 kD), detected by the zymography assay. MMP2 is a protease highly expressed by glioma cells and is responsible for cell invasion. Also that the EFEMP1 protein variant expressed from construct E5 significantly inhibits U251-NS glioma cell production of activated MMP2; whereas the wild-type EFEMP1 and EFEMP1 protein variants expressed from constructs E1, E15, and E18 significantly promotes U251-NS glioma cell production of activated MMP2.

Figure 5:
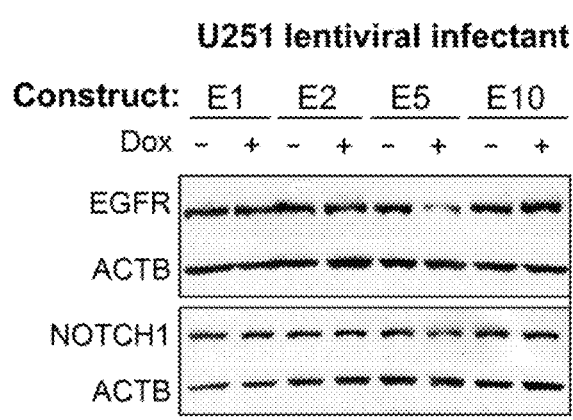
FIG. 5 is a photograph of immunoblots described in Example 7, conducted with parental culture U251 cells infected with the E1, E2, E5, and E10 pTRIPZ lentiviral constructs described in FIG. 2 and Example 1.

FIG. 5 is a photograph of immunoblots described in Example 7, conducted with parental culture U251 cells infected with the E1, E2, E5, and E10 pTRIPZ lentiviral constructs described in FIG. 2 and Example 1. Lentiviral infectants were cultured in medium containing doxycycline to induce transgene expression for 3 days, and expression was verified by assaying RFP expression with a fluorescent microscope. About 40% of gliomas overexpress EGFR, and EGFR activation is functionally related to enhanced cell survival and growth. Activation of Notch signaling by increasing NOTCH1 expression is a common feature of cancer stem cells. The results indicate that the EFEMP1 protein variant expressed from the E5 construct reduces the expression of EGFR and NOCTH 1 at protein level in U251 cells. ACTB expression level was used to indicate equal protein loading.

Figure 6:
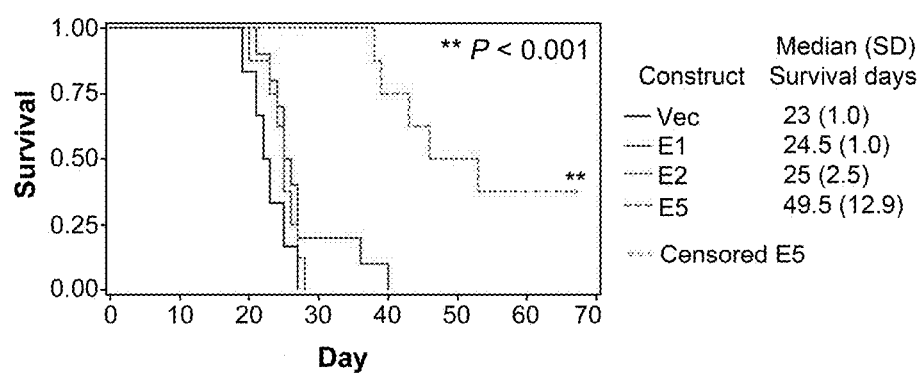
FIG. 6 is a survival plot for mice from the I.C. xenograft assay described in Example 8, initiated with neural sphere cultures of U251 cells infected with the E1, E2, and E5 pTRIPZ lentiviral constructs described in FIG. 2 and Example 1.

FIG. 6 is a Kaplan-Meier survival plot, carried out with mice from the intracranial xenograft assay described in Example 8, initiated with neural sphere cultures of U251 (U251-NS) cells infected with the E1, E2, and E5 pTRIPZ lentiviral constructs described in FIG. 2 and Example 1. Mice were fed with doxycycline-containing water from day 1 and throughout the experiment. RFP-expression was shown in the resulting tumors. The results indicate that the EFEMP1 protein variant expressed from the E5 construct inhibits tumorigenecity of U251-NS cells, measured by significantly prolonged survival, with median survival time more than doubled.

Taken together, the data and results set forth above indicate that the E5 EFEMP1 protein variant is a potent ETSP. The amino acid sequence of the FLAG tagged E5 EFEMP1 protein variant is set forth in SEQ ID NO 1. The amino acid sequences of a non-FLAG tagged E5 EFEMP1 protein variant is set forth in SEQ ID NO 2.

Example 1

EFEMP1 Deletion/Mutation Constructs.

Expression constructs encoding the E1, E2, E3, E4, E5, E6, E7, E8, E9, E10, E11, E13, E15, and E18 wild-type and variant EFEMP1 proteins illustrated in FIG. 2 and described above were made by PCR, with primers designed to create restriction sites for cloning and/or ligation of two separate cDNA fragments of EFEMP1. PCR products were cloned into TA-cloning vector pCR4.0 and sequence verified, prior to subcloning into mammalian expression vector pcDNA3.1+ (Life Technologies) and lentiviral vector pTRIPZ. A shuttle vector had been made to introduce internal ribosome entry site for expression of EFEMP1 wild-type and variant proteins in pTRIPZ (Thermo Scientific) under the same promoter for red fluorescent protein (RFP).

Example 2

U251 Lentiviral Infectants.

U251 (parental and neural sphere cultures) lentiviral infectants were established by generating lentivirus from co-transfecting HEK293 with plasmid DNA constructs (lentiviral vector pTRIPZ-empty vector or pTRIPZ-EFEMP1 construct E1, E2, E3, E4, E5, E6, E7, E8, E9, E10, E11, E13, E15, and E18 together with its derived constructs, psAX2, and pCMV-VSV-G). The U251 lentiviral infectants were established after elimination of uninfected cells by a 1-2 week culture under selecting antibiotic (1.25 µg/ml puromycin) and addition of doxycycline (1 µg/ml) to monitor success of infection via RFP expression in live cells with inverted fluorescent microscopy.

U251 Stable Transfectants.

U251 stable transfectants were established by transfecting with with plasmid DNA constructs (pcDNA3.1 vector or pcDNA-E1, E2, E3, E4, E5, E6, E7, E8, E9, E10, E11, E13, and E15), and cultured under selecting antibiotic (400 µg/ml neomycin) to form colonies. Individual colonies were picked using pipet tips, and transferred to 6-well plates to expand the colonies.

Example 3

Soft Agar Colony Formation Assay.

800-1000 cells were mixed with 1 ml of 0.3% soft agar in DMEM/F12 supplemented with 5% bovine serum or a mitogen supplement for NS cultures described in Example 10, spread onto hardened 0.5% soft agar in the same medium (1 ml per well in four corner wells of a 6-well plate). 1 ml of the same medium was added 2 and 3 weeks later and colony numbers were counted 4 weeks later under a microscope with a 4× lens. The cells were U251 control cells and U251 cells stably transfected with constructs E1, E2, E3, E4, E5, E6, E7, E8, E9, E10, E11, E13, E14, E15, or pcDNA-empty vector (Vec). The cells were cultured in medium containing doxycycline to induce transgene expression. Total number of colonies in each well were counted under microscope with 4× lens and normalized to average number of colony from Vec control (set in uninity). The average (Ave) and standard deviation (SD) were based on colonies formed 4 individual wells. 5-10 Representative colonies were measured and scaled by the diameter of the colony: 1+(~10 µm), 2+(~20 µm), 3+(30-40 µm), 4+(40-60 µm), 5+(50-100 µm), 6+(100-200 µm).

Example 4

Subcutaneous (S.C.) Xenograft Assay.

Parental cultures of U251HF lentiviral infectant cell lines pTRIPZ-vec and pTRIPZ-E1, E2, E5, E11, E13, E15, and E18 were grown in media containing 1 µg/ml doxycycline. $2.5 \times 10^6$ U251HF lentiviral infectant cells in 50 µl DMEM/F12 containing 14× diluted matrigel (original concentration 9-12 mg/ml) were subcutaneously injected into female nude mice (strain NCrNu-M, Taconic, Hudson, N.Y.) that were 4-6 weeks old, anterior to their right and left thighs on both sides. Injected mice were provided with water containing 1 µg/ml doxycycline the day of injection. Tumors were removed 25 days after injection, weighed, and analyzed by t-test (paired, two tailed).

Example 5

Matrigel Invasion Assay.

9-12 mg/ml Matrigel was thawed on ice or at 4° C. 10 ml ice cold serum free medium was added to the thawed matrigel. Plates were prepared by diluting thawed matrigel with ice cold SF-DMEM/F12, add 200 µl to transwell (12 well; 8 µm), and then incubating at room temp for >1 hour. Before plating cells, unbound material was gently aspirated off. The matrigel coating is colorless and not visible. Cells were prepared by detaching cells grown in 100 mm dishes to 80-90% confluency, by washing with 10 ml PBS, digesting with 2 ml 0.05% trypsin-EDTA for 30 sec, removing the trypsin, detaching the cells by tapping the bottle, then adding 10 ml culture medium and pipetting up and down, and then transferring the cells to a 15-ml tube. The cells were then spun down, resuspended in 10-15 ml SF-medium, taking 10 µl to count cells with a hemocytometer. $5 \times 10^6$ cells were then spun down and resuspended in 5 ml SF-medium at $1 \times 10^6$/ml. $5 \times 10^5$ cells were added to coated transwell, and 1 ml 0.05% CS-medium was added to the to bottom well. Plating was done in a $CO_2$ incubator, where plates were then cultured for 24 hours.

Cells that penetrated the matrigel were stained with HEMA3 CMS as follows. 0.5 ml of fixative stain was added to the well of the plate and 0.2 ml was added to the transwell. The stain was removed after 20 minutes. Then, 0.5 ml of red stain was added to the well of the plate and 0.2 ml was added to the transwell. The stain was removed after 20 minutes. Then, 0.5 ml of dark blue stain was added to the well of the plate and 0.2 ml was added to the transwell. The stain was removed after 20 minutes. A Q-tip dipped in water was used to remove the matrigel membrane, which was then air dried. The dry membrane was placed on a slide and mounting medium was added. A coverslip was then placed on top, and 10 pictures were taken for each filter with a microscope using a 20× lens. Cells were then counted based on the pictures taken, compared to control (Vec), which was set to unity, and analyzed by t-test (paired, two tailed).

Example 6

Gelatin Zymography Assay.

Conditioned medium of NS cultured U25F lentiviral infectant cells expressing wild-type EFEMP1 and variant EFEMP1 protein from constructs pTRIPZ-E1, E2, E5, E13, E15, or E18 cells, as well as NS culture U251HF control, pTRIPZ-vec cells, were grown for 48 hours in serum-free DMFM/F12 media containing 1 µg/ml doxycycline were collected as follows. Cells were spun down, and 0.3 ml supernatant was transferred into a 1.5 ml tube. Protein was precipitated from the supernatant by adding 1.2 ml cold acetone. The precipitate was spun immediately at 14K RPM for 5 min at 4° C. Condition medium protein (CM-P) was resuspended in 100 µl 1×RIPA+1× protease inhibitor cocktail. 2 µl of CM-P was taken to determine protein concentrate with a BIO-RAD Protein Assay. The resuspended CM-P was stored at 80° C.

2-4 µg of CM-P were mixed with, 1×RIPA, and 2× sample buffer (100 µl 10% BB, 10 ml glycerol, 1 g SDS, 7.5 ml 1 M Tris.HCl pH 6.8, add sterile ddH2O to 50 ml), briefly spun, and loaded onto a zymogrpahy gel in 1× Tris-glycine-SDS running buffer. The gel was run at room temp @90 V for 2 hours. The gel was washed several times in 2.5% Triton X-100 for 1-2 hour at RT with gentle shaking. The gel was then incubated overnight at 37° C. in protease reaction buffer (50 mM Tris (pH=7.5), 10 mM $CaCl_2$, 150 mM NaCl). The gel was then stained for 30 min with Coomassie Blue R-250 (0.1% coomassie blue, 10% acetic acid, 10% isopropanol in ddH2O) with gentle shaking. The gel was then the stained in 10% acetic acid, 30% methanol solution three times for 20 minutes, and air-dried overnight between two cellophane papers.

Example 7

Immunoblotting.

30-40 µg protein of whole cell lysate were loaded onto 8% SDS-PAGE gel in 1× Tris-glycine-SDS running buffer. The gel was run at room temp, 90 V for 2 hours, and transferred to A nitrocellular membrane. The blots were blocked with 5% skim milk for 1 hour, then incubated in 1% BSA containing rabbit primary antibodies for EGFR (1:1000 dilution) or NOTCH1 (1:1000 dilution) overnight. Then washed with 1× TBST for 1 hour, incubated with anti-rabbit IgG HRP-conjugated secondary antibody (1:10,000 dilution) for 1 hour. An ECL detection kit was used to develop the signal in the immunoblots.

Example 8

Intracranial (I.C.) Xenograft Assay.

Glioma cells ($1 \times 10^5$/3 µl DMEM/F12) were injected into the frontal lobe of 4-6 week old, female, nude mice (strain NCrNu-M, Taconic, Hudson, N.Y.), following IACUC approved surgical procedures. After I.C. implantation, mice were daily observed for moribund signs (hunchback posture, marked weight loss, and gait impairment) and periodically weighed. Mice were euthanized when they developed brain-damage symptoms (ataxia, hemiparesia, etc) and/or 20% body weight loss, and the following day was recorded as the survival date for survival analysis.

Example 9

Parental Culture of U251.
U251 cells were cultured in regular tissue-culture-treated dishes, in DMEM/F12 medium supplemented with 5% bovine serum and 1× penicillin-streptomycin, at 37° C. with 5% $CO_2$, in humidity chamber.

Example 10

NS Culture of U251.
U251 cells were cultured in an agar (1%)-coated dish, with DMEM/F12 medium supplemented with 20 ng/ml EGF, 20 ng/ml bFGF, 0.3% B27, and 1× penicillin-streptomycin, at 37° C. with 5% $CO_2$, in a humidity chamber.

The following publications are hereby incorporated by reference in their entirety:

Lecka-Czernik B, Lumpkin C K Jr, Goldstein S. An over-expressed gene transcript in senescent and quiescent human fibroblasts encoding a novel protein in the epidermal growth factor-like repeat family stimulates DNA synthesis. Mol Cell Biol. 1995 January; 15(1):120-8.

Sun B S, Zhu X, Clayton M M, Pan J, Feitelson M A. Identification of a protein isolated from senescent human cells that binds to hepatitis B virus X antigen. Hepatology. 1998 January; 27(1):228-39.

Lissemore J L, Starmer W T. Phylogenetic analysis of vertebrate and invertebrate Delta/Serrate/LAG-2 (DSL) proteins. Mol Phylogenet Evol. 1999 March; 11(2):308-19.

Stone E M, Lotery A J, Munier F L, Héon E, Piguet B, Guymer R H, Vandenburgh K, Cousin P, Nishimura D, Swiderski R E, Silvestri G, Mackey D A, Hageman G S, Bird A C, Sheffield V C, Schorderet D F. A single EFEMP1 mutation associated with both Malattia Leventinese and Doyne honeycomb retinal dystrophy. Nat Genet. 1999 June; 22(2):199-202.

Marmorstein L Y, Munier F L, Arsenijevic Y, Schorderet D F, McLaughlin P J, Chung D, Traboulsi E, Marmorstein A D. Aberrant accumulation of EFEMP1 underlies drusen formation in Malattia Leventinese and age-related macular degeneration. Proc Natl Acad Sci USA. 2002 Oct. 1; 99(20):13067-72

Klenotic P A, Munier F L, Marmorstein L Y, Anand-Apte B. Tissue inhibitor of metalloproteinases-3 (TIMP-3) is a binding partner of epithelial growth factor-containing fibulin-like extracellular matrix protein 1 (EFEMP1). Implications for macular degenerations. J Biol Chem. 2004 Jul. 16; 279(29):30469-73.

Albig A R, Neil J R, Schiemann W P. Fibulins 3 and 5 antagonize tumor angiogenesis in vivo. Cancer Res. 2006 Mar. 1; 66(5):2621-9.

Fu L, Garland D, Yang Z, Shukla D, Rajendran A, Pearson E, Stone E M, Zhang K, Pierce E A. The R345W mutation in EFEMP1 is pathogenic and causes AMD-like deposits in mice. Hum Mol Genet. 2007 Oct. 15; 16(20):2411-22.

McLaughlin P J, Bakall B, Choi J, Liu Z, Sasaki T, Davis E C, Marmorstein A D, Marmorstein L Y. Lack of fibulin-3 causes early aging and herniation, but not macular degeneration in mice. Hum Mol Genet. 2007 Dec. 15; 16(24):3059-70.

Yue W, Dacic S, Sun Q, Landreneau R, Guo M, Zhou W, Siegfried J M, Yu J, Zhang L. Frequent inactivation of RAMP2, EFEMP1 and Dutt1 in lung cancer by promoter hypermethylation. Clin Cancer Res. 2007 Aug. 1; 13(15 Pt 1):4336-44.

Invitrogen; pcDNA™3.1(+) pcDNA™3.1(−); Catalog nos. V790-20 and V795-20; Version K, 10 Nov. 2010 28-0104; User Manual.

Thermo Scientific Open Biosystems Expression Arrest TRIPZ Lentiviral shRNAmir; Technical Manual.

Although the disclosure has been provided in the context of certain embodiments and examples, it will be understood by those skilled in the art that the disclosure extends beyond the specifically described embodiments of polypeptide and nucleic acid sequences. Accordingly, the disclosure is exemplary and not intended to be limited by the specific disclosures of embodiments herein.

What is claimed is:

1. An isolated polypeptide comprising SEQ ID NO:1.
2. An isolated nucleic acid molecule that encodes the polypeptide of claim 1.
3. The isolated nucleic acid molecule of claim 2, wherein the isolated nucleic acid molecule is DNA.
4. An isolated polypeptide comprising an amino acid sequence having at least 95% identity to SEQ ID NO: 1, wherein the amino acid at position 218 relative to SEQ ID NO: 1 is aspartic acid and wherein the polypeptide suppresses U251 cell growth.
5. An isolated nucleic acid molecule that encodes the polypeptide of claim 4.
6. The isolated nucleic acid molecule of claim 5, wherein the isolated nucleic acid molecule is DNA.
7. An isolated polypeptide comprising SEQ ID NO: 2.
8. An isolated nucleic acid molecule that encodes the polypeptide of claim 7.
9. The isolated nucleic acid molecule of claim 8, wherein the isolated nucleic acid molecule is DNA.
10. An isolated polypeptide comprising an amino acid sequence having at least 95% identity to SEQ ID NO: 2, wherein the amino acid at position 210 relative to SEQ ID NO: 2 is aspartic acid and wherein the polypeptide suppresses U251 cell growth.
11. An isolated nucleic acid molecule that encodes the polypeptide of claim 10.
12. The isolated nucleic acid molecule of claim 11, wherein the isolated nucleic acid molecule is DNA.

* * * * *